(12) United States Patent
Durette

(10) Patent No.: US 10,632,016 B2
(45) Date of Patent: Apr. 28, 2020

(54) DISPOSABLE EYE PATCH/SHIELD

(71) Applicant: Oculo-Plastik, Inc., Montreal (CA)

(72) Inventor: Jean-Francois Durette, Montreal (CA)

(73) Assignee: OCULO-PLASTIK, INC., Montreal, Quebec (CA)

(*) Notice: Subject to any disclaimer, the term of this patent is extended or adjusted under 35 U.S.C. 154(b) by 755 days.

(21) Appl. No.: 15/215,242

(22) Filed: Jul. 20, 2016

(65) Prior Publication Data

US 2017/0027757 A1 Feb. 2, 2017

Related U.S. Application Data

(60) Provisional application No. 62/198,743, filed on Jul. 30, 2015.

(51) Int. Cl.
*A61F 9/04* (2006.01)
*A61B 90/00* (2016.01)

(52) U.S. Cl.
CPC ............. *A61F 9/04* (2013.01); *A61B 90/04* (2016.02); *A61B 2090/049* (2016.02); *A61F 2220/0008* (2013.01); *A61F 2250/0047* (2013.01)

(58) Field of Classification Search
CPC . A61F 9/04; A61F 9/045; A61F 13/12; A61B 90/04; A61B 2090/0436; A61B 2090/0445; A61B 2090/0454; A61B 2090/049
USPC ............. 128/858; 428/41.7, 41.8, 42.1, 42.2, 428/42.3; 206/505, 506, 507, 509, 515, 206/516, 517, 519, 520
See application file for complete search history.

(56) References Cited

U.S. PATENT DOCUMENTS

| 1,715,685 A * | 6/1929 | Tighe .................. B65D 5/5035 206/516 |
| 3,068,863 A | 12/1962 | Bowman et al. |
| 3,092,103 A | 6/1963 | Mower |

(Continued)

FOREIGN PATENT DOCUMENTS

| DE | 2605275 | 8/1976 |
| EP | 0037521 | 10/1981 |

(Continued)

OTHER PUBLICATIONS

Written Opinion of the International Searching Authority dated Aug. 2, 2017 for counterpart PCT Application No. PCT/CA2016/050873.

(Continued)

*Primary Examiner* — Tarla R Patel
(74) *Attorney, Agent, or Firm* — Shuttleworth & Ingersoll, PLC; James C. Nemmers

(57) ABSTRACT

A shield for protecting the eye of a patient who is undergoing treatment of a facial area, such as the nose-bridge, forehead, temple, or an area immediately surrounding the eye. The shield has an outer shell of a formed semi-flexible or rigid metal foil that extends all the way to the edge of the shield, including an adhesive area of the shield that holds the shield around the eye of the patient. The foil layer is combined with one or more layers of polyester to avoid reflection of the light energy on the user or one or more layers of foam to provide for heat insulation, adhesion and patient comfort. The shield is formed at the contact portion to fit over the orbital area of the patient's eye.

5 Claims, 8 Drawing Sheets

(56) References Cited

U.S. PATENT DOCUMENTS

| | | |
|---|---|---|
| 4,635,625 A | 1/1987 | Teeple |
| 4,682,371 A | 7/1987 | Heitman |
| 4,867,146 A | 9/1989 | Krupnick et al. |
| 4,951,658 A | 8/1990 | Morgan et al. |
| 4,969,472 A * | 11/1990 | Langley .................... A61F 9/04 128/858 |
| 5,004,333 A | 4/1991 | Bruhl |
| 5,180,360 A | 1/1993 | Rhame, Jr. |
| 6,131,208 A * | 10/2000 | Banks ...................... A61F 9/04 128/858 |
| 6,945,936 B1 * | 9/2005 | Kerr ........................ A61B 3/16 374/158 |
| RE39,896 E | 10/2007 | Arnold et al. |
| 7,584,754 B1 | 9/2009 | Pellegrini et al. |
| 2008/0148461 A1 * | 6/2008 | Guyuron .................. A61F 9/04 2/15 |
| 2008/0234707 A1 * | 9/2008 | Muehlhoff .......... A61F 9/00827 606/166 |
| 2011/0004969 A1 | 1/2011 | Frohlich |
| 2014/0250556 A1 * | 9/2014 | Awan ....................... A61F 9/04 2/15 |

FOREIGN PATENT DOCUMENTS

| | | |
|---|---|---|
| WO | WO2005053585 | 6/2005 |
| WO | WO2007069534 | 6/2007 |

OTHER PUBLICATIONS

International Preliminary Report on Patentability dated Nov. 22, 2017 for counterpart PCT Application No. PCT/CA2016/050873.
Written Opinion of the International Searching Authority dated Sep. 29, 2016 for counterpart PCT Application No. PCT/CA2016/050873.

* cited by examiner

US 10,632,016 B2

DISPOSABLE EYE PATCH/SHIELD

This application claims priority under 35 USC 119 to Provisional Patent Application No. 62/198,743 filed on Jul. 30, 2015 the contents of which are hereby incorporated by reference.

FIELD OF THE INVENTION

This invention relates to a disposable eye patch/shield. In particular, this invention relates to a disposable eye patch/shield used during surgical and/or professional facial care procedures.

BACKGROUND OF THE INVENTION

Cosmetic surgical procedures (e.g., plastic surgery) and professional facial care procedures are becoming increasingly popular. In some cases, patients request such procedures for treatments to such facial areas as the nose-bridge, forehead, temples, and areas immediately surrounding the eyes. In performing surgical or other procedures to such areas of the faces, the procedures often require very delicate and detailed work, and therefore doctors and other professionals must have access to as much unobstructed area as possible. At the same time, the doctors or other professionals need to avoid the possibility of damaging the patient's eyes when using various surgical, medical and cosmetic items and procedures, such as lasers, intense pulse light (IPL), light emitting diodes (LED), Radio Frequency (RF), ultrasounds, abrasion systems, chemicals, air jets, air streams, liquids, medicines, medicine applicators, surgical tools (e.g., scalpels, hemostats, needles, etc.) and other devices. Therefore, the patient's eyes are typically covered by materials such as surgical tape and gauze while a surgical or facial care procedure is being performed. However, professionals are finding an increased need for more complete access to areas around the patient's eyes, and therefore require more reliable protection methods and devices for the patient's eyes.

U.S. Pat. No. 4,682,371 to Heltman discloses a protective eye patch. This eye patch has several adhesive tabs for securing an eye patch to protect the patient's eye. However, since the tabs do not seal the entire edge of the eye patch around the eye, there is a possibility that liquids or medicines may enter a patient's eye covered by this eye patch.

U.S. Pat. No. 3,068,863 to Bowman discloses another type of protective eye patch. This eye patch is designed always to keep the eye closed. However, since this patch is adhered onto the patient's eyelid as well as surrounding eye tissues, this eye patch is not comfortable to wear, and this is the only option for this patch.

U.S. Pat. No. 3,092,103 to Mower provides an eye patch that has a cushion material on an edge of the eye patch which allows a patient's eye to move and/or open underneath the eye patch. Because of its large size, this patch is not suitable for many surgical and facial care procedures which require a larger working area for the surgeon.

U.S. Pat. No. 4,867,146 to Krupnick et al. discloses an eye patch for preventing opening of an eye and preventing corneal abrasion. This eye patch has adhesive areas around the patch and part of a center part of the eye patch. However, because of the adhesive areas in the center part, it is uncomfortable for the patient to wear, and, in fact, it is designed for use on an anesthetized patient.

U.S. Pat. No. 5,180,360 to Rhame, Jr. discloses an oval shaped eye patch with a thick inner foam patch or adjustable bladder for adjusting pressure against an eyelid. It is intended to work with all energy sources that are employed in procedures that utilize medical treatment lights and even hybrid systems with light and electrical current energy units. However, this patch is quite large, being designed to attach to the outside of the eye socket, and covers some areas of the face that may need to be accessed for some surgical or facial care procedures.

U.S. Pat. No. 7,584,754 to Pellegrini and Krupnick discloses a patch with a single metallic layer with one or two foam sheet members that are flat. In this patent, the foam is always exposed to a laser and the eye is in contact with the metallic layer in one version.

There is therefore a need for an improved eye shield that will provide protection for the eye during any type of surgical or facial care procedure while not interfering with the particular procedure being conducted by the health care professional. The shield must also be comfortable for the patient, even though the eyelid may be open or closed.

SUMMARY OF THE INVENTION

The eye shields of the invention are made using an outer layer of a flat or formed, semi-flexible or rigid metal foil that extends all the way to the edge of the shield, including the adhesive area of the shield that adheres to the patient. The foil layer may be combined with one or more layers of polyester foam to avoid reflection to the user or to provide for heat insulation, adhesion and patient comfort. The shield is flat or curved to the extent necessary at the contact portion to fit over the orbital area of the patient's eye. A release layer covering the adhesive is open to allow for stacking of the curved versions of the shields until ready for use.

DESCRIPTION OF THE PREFERRED EMBODIMENTS

Referring to FIGS. 1-6 of the drawings, the basic structure of the eye shield of the invention is a semi-flexible or rigid shell 10, preferably made from a material of some metal, such as aluminum. The shell 10 can be pure metal or metal coated with some suitable material, such as polyester or foam, but not limited to polyester or foam, on top or on both sides, as shown in the various embodiments described herein. This is so the shield can be used when shielding both a light energy beam and electrical currents. Some energy skin treatment units on the market come both with an electrical current (radio frequency (RF), and a light energy, like laser, IPL, etc. Ideally, the shell 10 will protect against units with electrical currents, such as RF, but will also protect against energies in addition to RF. The shell 10 must also withstand some energy exposure from a light beam source, such as a laser beam to be safely used as a shield. The metallic shell 10 is formed in any suitable manner to the desired shape, preferably a rounded oval, to fit within the eye socket of a patient to be treated but of a sufficient size to always cover the patient's eye. Thus, the shell 10 is shaped to fit well over the orbital rim or just inside the orbital rim of most patients. If the shield is formed from aluminum foil which is quite thin, the shell 10 will be more or less flexible and will allow for some minor adjustments after placement on the patient's orbit. If the foil is thicker, it will be less adjustable. The flexible or rigid shell 10 may also be flat or have a curvature that can vary depending upon the desired characteristics and uses for the eye shield as described hereinafter. The drawings show a moderately curved shape, but it should be understood that a flat or higher or lower curvature may be used. The higher curvature offers freedom for the eyelids and eye lashes to move when the shield is in place since a bulging cup will not touch normal eyelashes or the patient's eyelids. A curved shell is intended to be much more comfortable as there will not be any pressure on the eyelids and eyes, unless it is desired by the health care professional to keep the eyelids closed during a particular treatment by using a less curved or flat surface.

Figure 9:
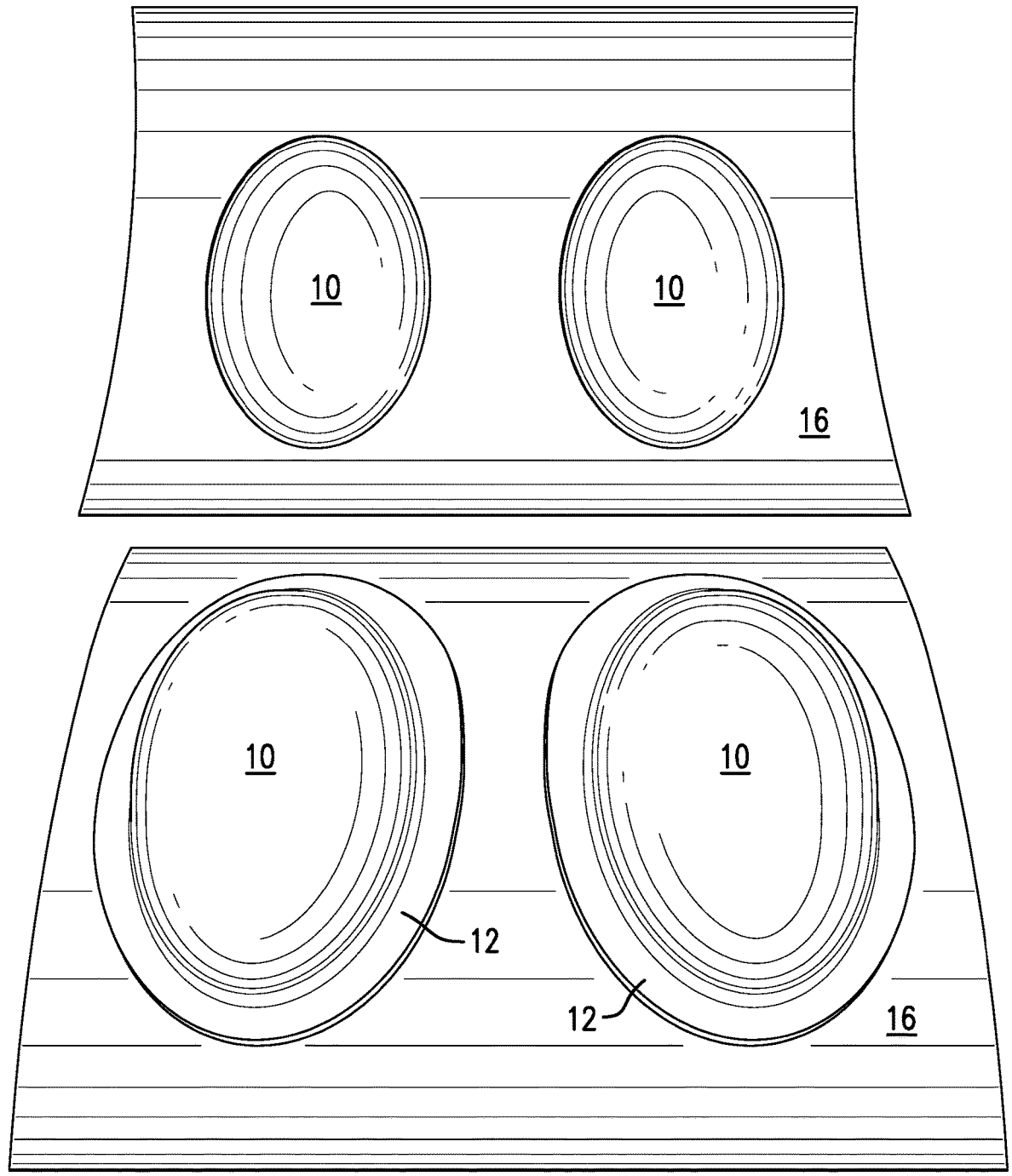
FIG. 9 is a perspective view of two pairs of shields ready to be stacked.
Figure 10:
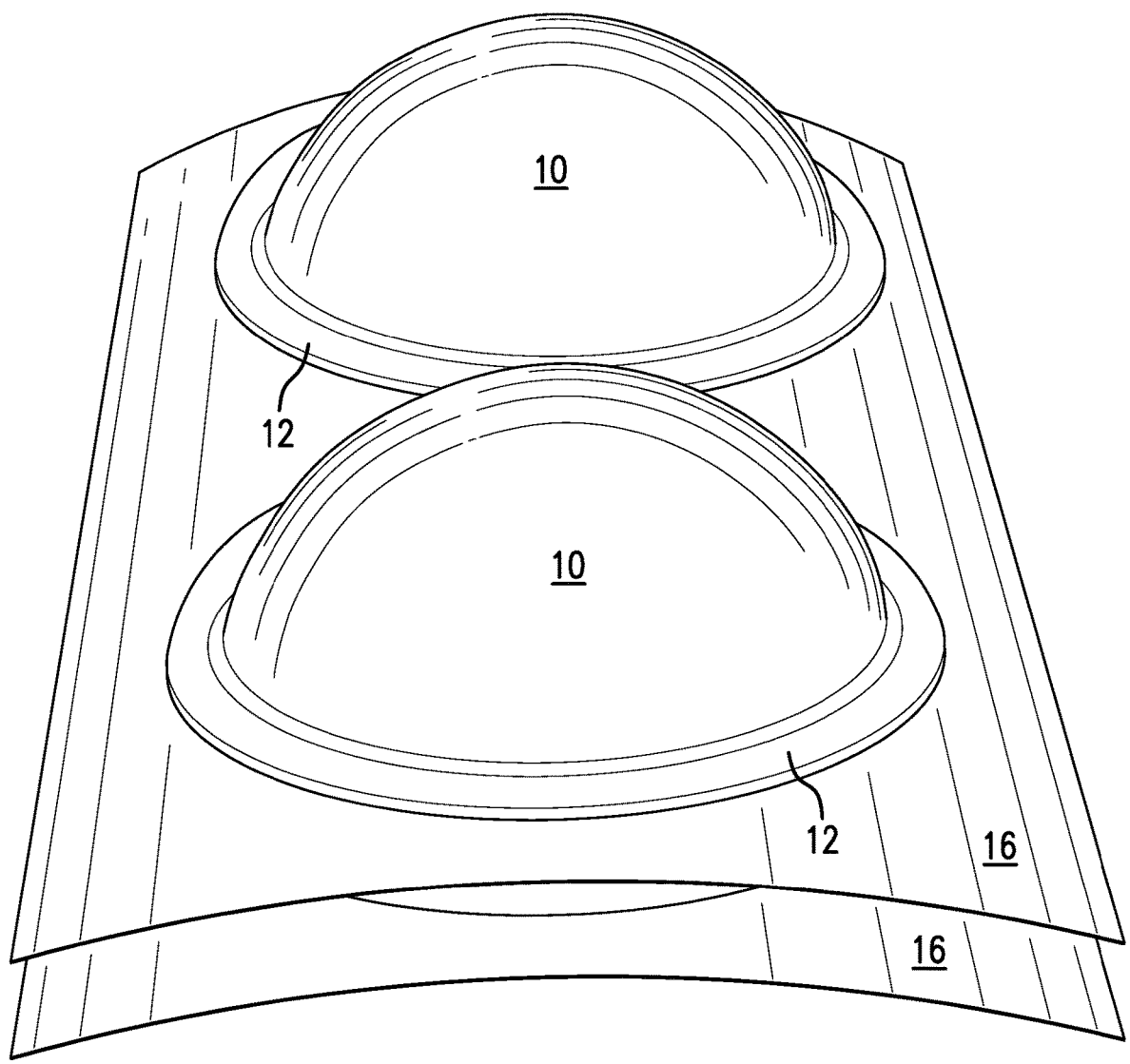
FIG. 10 is a perspective view showing the two pairs of shields of FIG. 9 stacked.

In most applications and in all the embodiments shown herein, the metallic shell 10 has an outwardly and somewhat downwardly extending peripheral rim or edge 12 to provide for additional patient protection. In the first embodiment illustrated in FIGS. 1-6, the metallic shell 10 is bare on both sides, i.e., shell 10 has no insulating layer, except that the peripheral edge 12 has adhered to its underside surface a foam layer 14 that extends around substantially the entire edge 12. The foam layer 14 contacts the patient's skin when the shell 10 is in place over the patient's eye. This foam layer 14 insulates the patient from heat or RF current if used by the health care professional. A suitable adhesive is applied to the underside of the foam layer 14 for the purpose of securing the eye shield to the patient. Attached to the adhesive side of the foam layer 14 is a release paper layer 16 that protects the adhesive on the foam layer until the shield is ready to be used. The layer 16 is removed when the user is ready to install the shield on a patient. The release paper layer 16 can be the same size as the edge 12 of the shield 10 or the paper layer 16 can extend beyond the edge 12. In the drawings, release paper layer 16 is shown as extended beyond the oval shape of the edge 12 of shield 10 to make it easier to remove the release paper layer 16. Both the foam layer 14 and release paper layer 16 are ring-shaped with their center part cut out so that the layers cover only the peripheral edge 12 of the shell 10 and do not extend inside the edge 12 of the shell 10. This allows stacking of the shields on top of each other (as illustrated in FIGS. 9 and 10). Once stacked, the shields can be placed in a box for shipping and storage until use. In the alternative, the paper layer 16 can extend across the opening of the shell 10 but simply be cross-cut in the center so it will not rip during production while still allowing the shield to be stacked. With the design of this first embodiment, the patient's eyelid would not be affected by the shield, and the patient can open and close the eyes as the rounded form of the shield gives some space over the eyelid.

Figure 1:
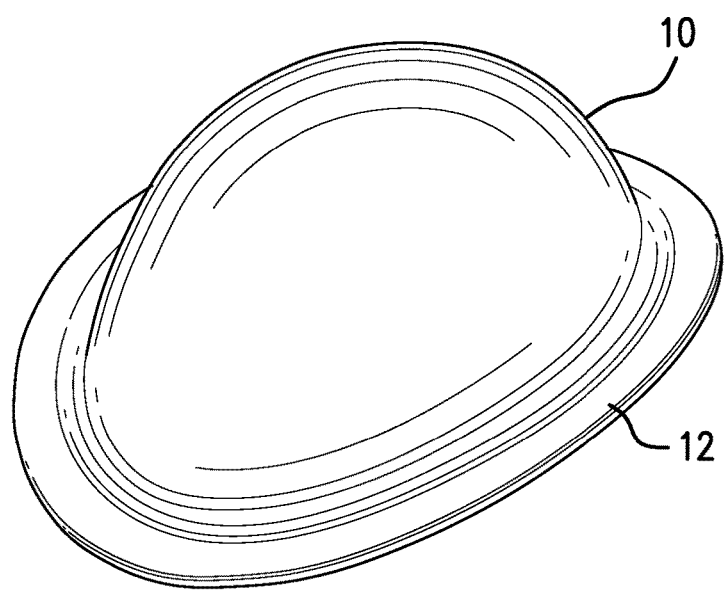
FIG. 1 is a perspective view of an eye shield according to the invention.
Figure 2:
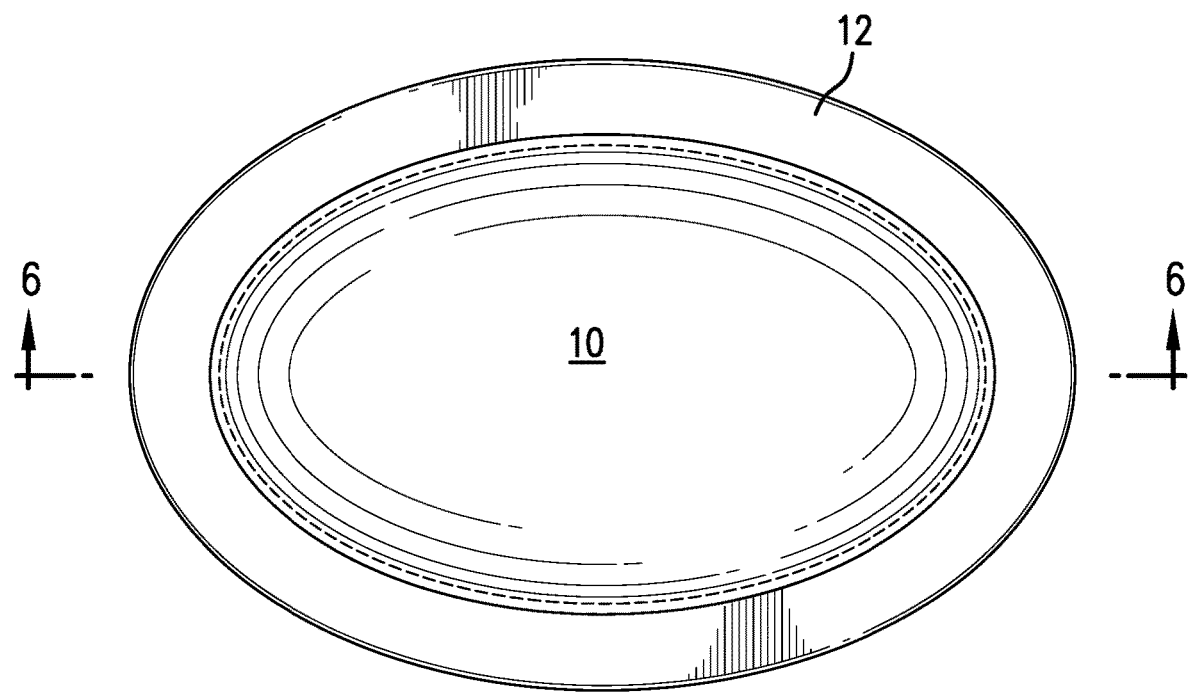
FIG. 2 is a bottom plan view of the eye shield.
Figure 3:
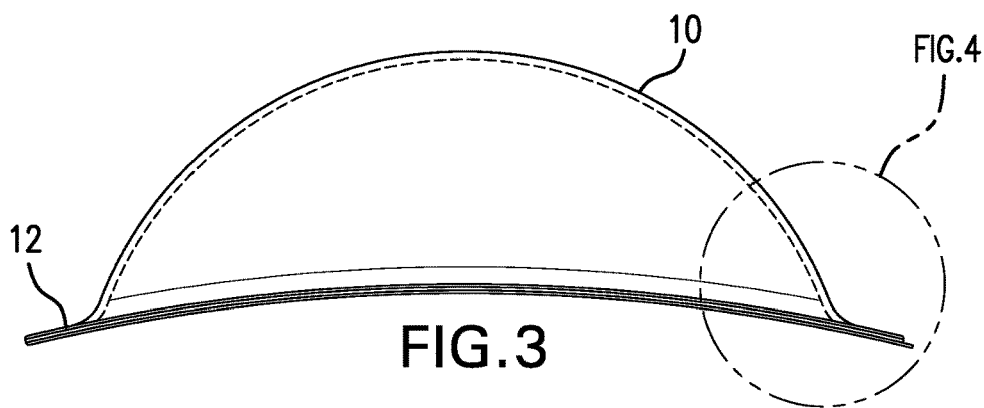
FIG. 3 is a side view of the eye shield of FIGS. 1 and 2.
Figure 4:
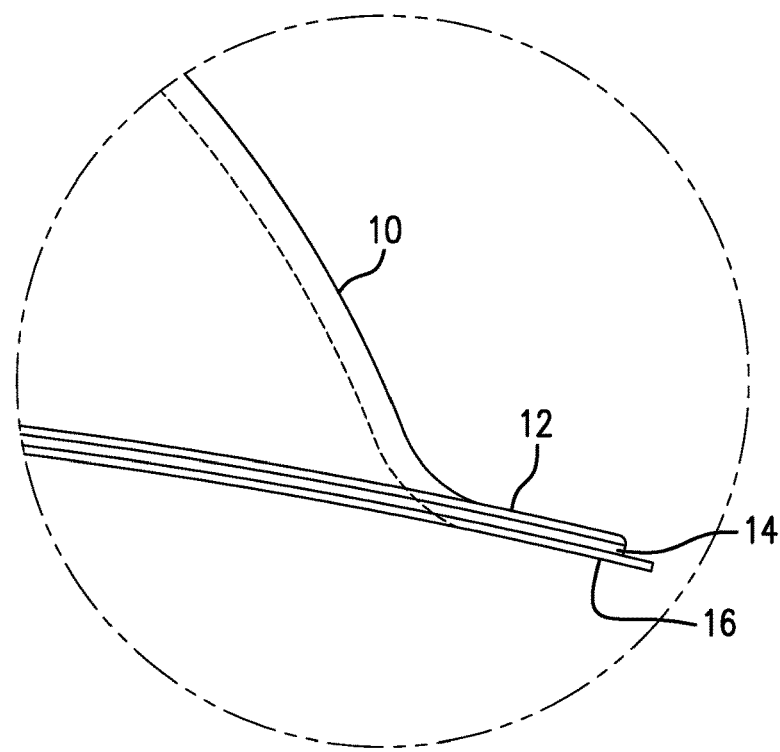
FIG. 4 is an enlarged view of a portion of FIG. 3.
Figure 5:
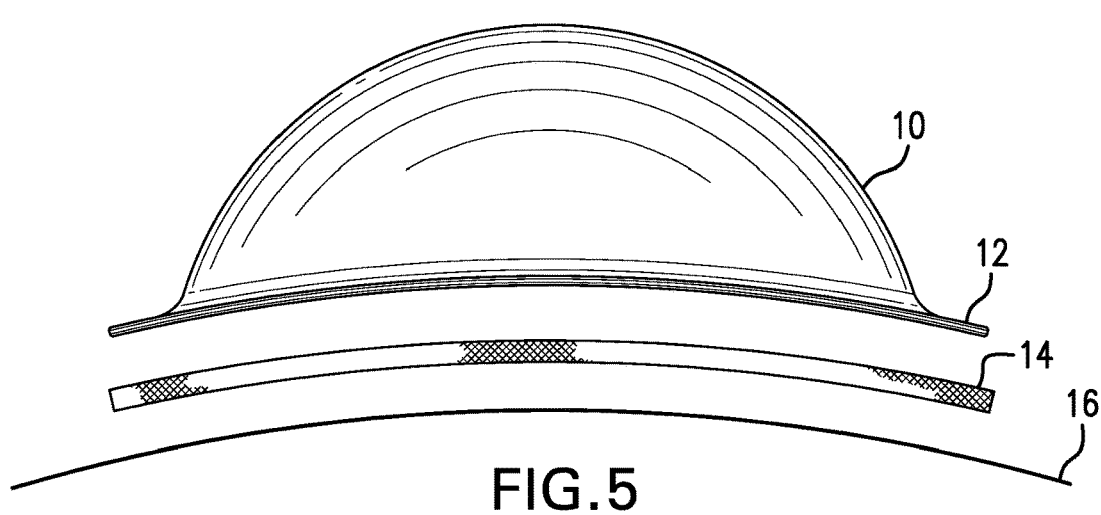
FIG. 5 is a side view similar to FIG. 3 but showing the layers of the shield separated.
Figure 6:
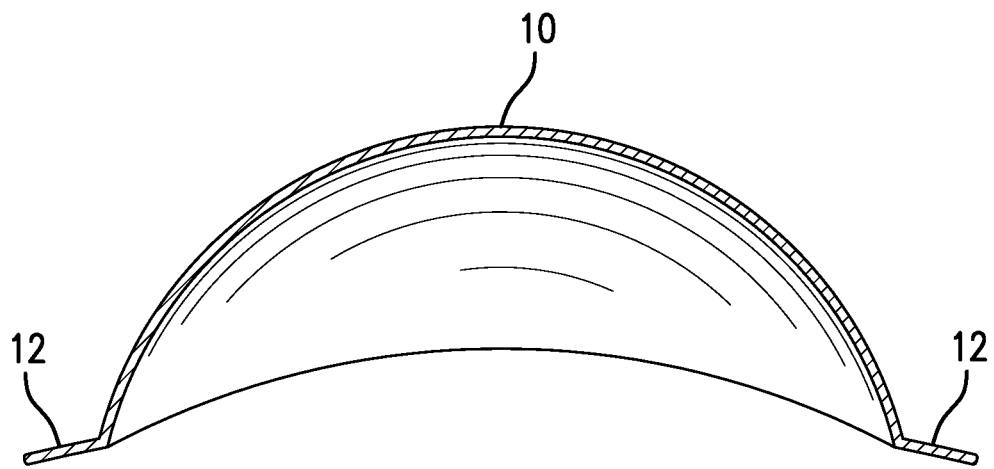
FIG. 6 is a sectional view of the eye shield taken on the line 6-6 of FIG. 2 but showing the layers separated.
Figure 6:
Figure 6:
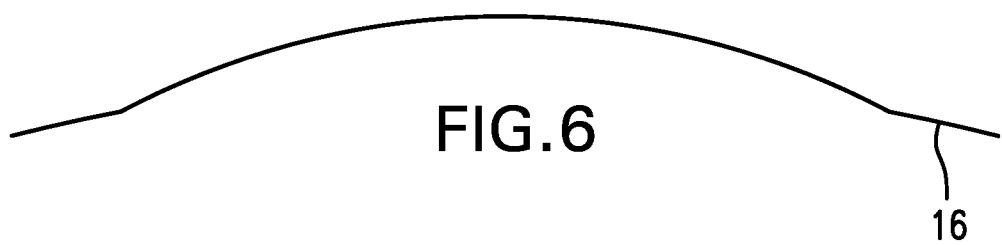
Figure 6A:
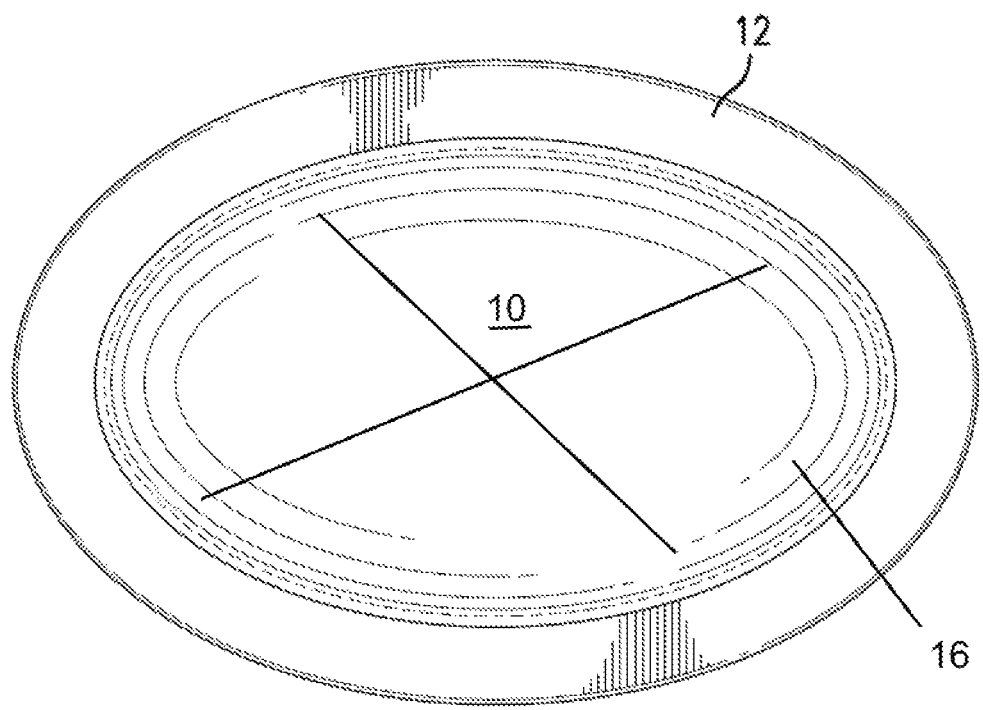
FIG. 6A is a bottom plan view of the eye shield similar to FIG. 2 but showing the center of the paper layer cross-cut.
Figure 7:
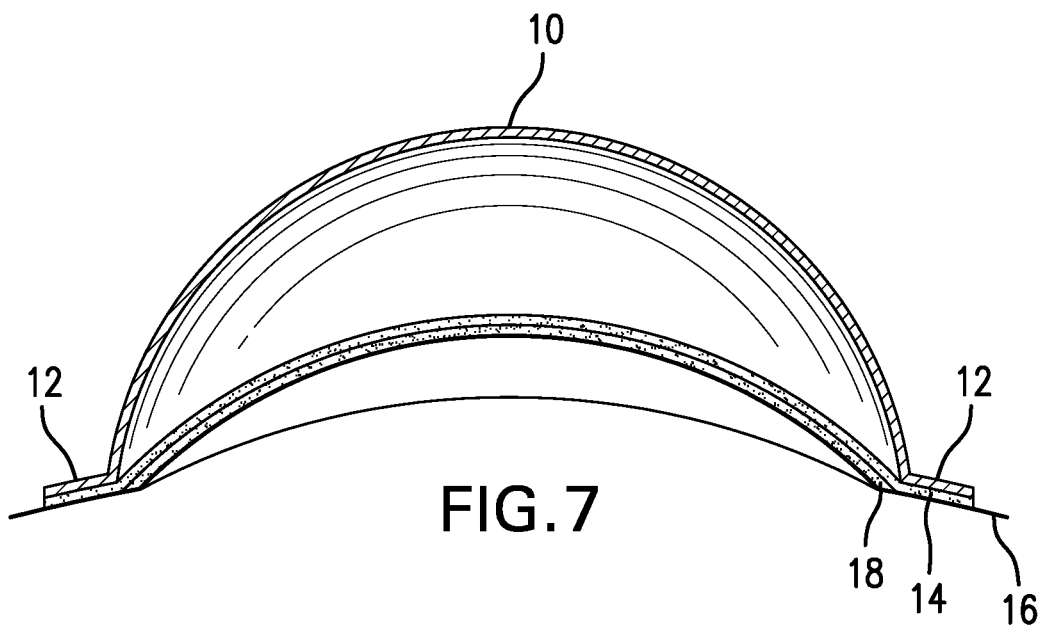
FIG. 7 is a sectional view similar to FIG. 6 but illustrating a second embodiment of the invention.

In a second embodiment of the invention illustrated in FIG. 7, the foam layer 14 is not cut out in the center but rather extends across the entire interior of the shell 10. This foam layer 14 provides additional insulation from the energy being used during a particular procedure. As shown in FIG. 7, the foam layer 14 can be spaced from the interior surface of the shell 10. The amount of spacing of foam layer 14 from the interior surface of the shell depends upon whether or not the shield is intended to press the patient's eyelid closed when the shield is in place. As shown, the foam layer 14 extends across the peripheral edge 12 and it glued to edge 12 to hold the foam layer in place. The release paper layer 16 also extends across the interior of the shell 10, covering the foam layer 14 and preferably extending beyond the edge 12. This embodiment is used when it is desired to press the eyelid closed when the shield is in place over the patient's eye without the foam layer 14 adhering to it, which may be more comfortable for the patient, especially when removing the shield after treatment. As an option, to provide more insulation where needed, the thickness of the foam layer 14 may be increased by the addition of a second foam layer 18, as illustrated in FIG. 7. Preferably, as shown in FIG. 7, the second foam layer 18 does not cover the peripheral edge 12. If desired, the entire bottom surface of the foam layer 18 may be coated with an adhesive, so that the layer 18 would adhere to the patient's eyelid. This may be desired in some instances where the health care profession wishes the patient to keep the eyelids closed during treatment. Of course, the shields of this embodiment could not be stacked in a package because the layers 14 and 16 extend across the entire opening of the bottom of the shell 10.

Figure 8:
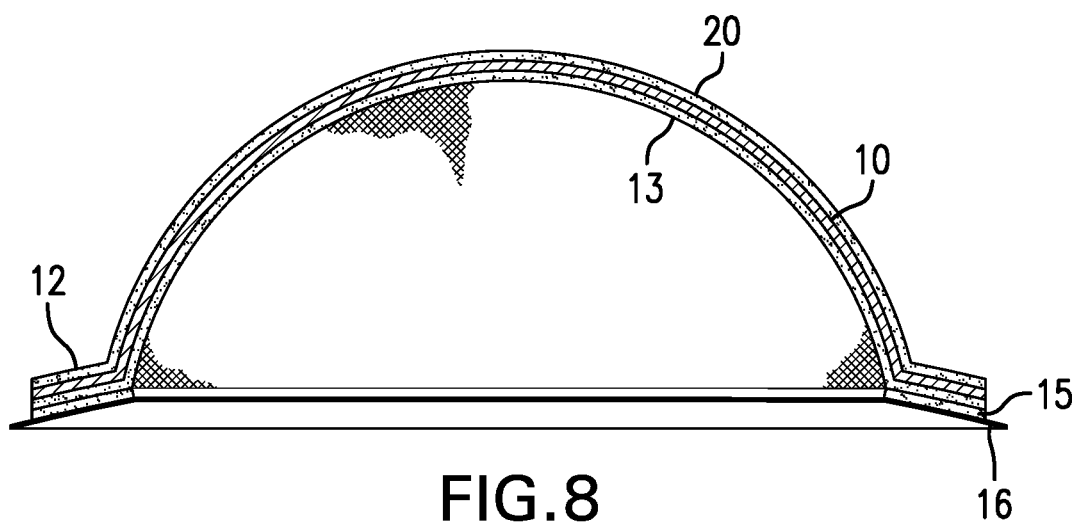
FIG. 8 is a sectional view similar to FIG. 7 but illustrating another embodiment of the invention.

FIG. 8 illustrates yet another embodiment in which an additional foam layer 20 is added to the shield by gluing a foam layer 20 to the exterior of the metallic shell 10. In addition, a first foam layer 13 extends over the entire inner surface of the shell 10 as well as the peripheral edge 12 and is glued to those surfaces. A second foam layer 15 is ring-shaped and extends only around the peripheral edge 12 and is glued to the foam layer 13. The exposed underside of the foam layer 15 is covered by the release paper 16 which is ring-shaped and extends only around the peripheral edge 12. The additional foam layer 20 applied to the exterior of the metallic shell 10 is used primarily where the light energy or RF system being used to treat the patient requires this additional insulation. Similar to the embodiment of FIGS. 1-6, the shield of this embodiment is open on the underside, so that the shields are stackable. FIGS. 9 and 10 illustrate how the shields might be stacked. Two pairs of shields are shown with a single release paper 16 joining each pair of shields. FIG. 10 shows the pairs stacked.

In all the embodiments of the invention, the basic design of the shield allows the shield to be smaller than know shields. The metallic shell 10 is entirely of protective foil or contains a metallic substance and covers the entire eye but never touches the patient's skin. One or more of the foam layers is always beneath the metallic shell 10. The foam layer may be ring-shaped to cover only the peripheral edge 12, or one or more foam layers may be included to insulate the patient's skin from any excessive heat generated during the treatment by the professional. The additional foam layer(s) may be on top of the metallic shell only, or inside the shell only, or on both sides of the shell. In any case, there will always be at least a ring-shaped foam layer covered by a release paper to adhere the shield to the patient. Color coding of the shields may be used to differentiate shields of different sizes or types. In the preferred embodiments, the shields are designed to be stackable to facilitate shipping and storage until ready for use.

The selection of the proper type and size of the shield by the health care professional is very important. For example, if the shield is too large for a particular patient, the patient can freely open the eyes, and if the energy source is very potent, like a Yag laser, and the patient does not listen to the instructions given by the professional to close their eyes, or the professional forgets to give the instructions, a patient's retina or cornea could be damaged. The invention provides different shield sizes and designs for differences in patient anatomy and for different treatments, and with color coding of the shields and other proper warnings, possible damage to the patient's eyes can be greatly minimized.

The terms and expressions which have been used in this specification are used as terms of description and not of limitation. There is no intention in the use of such terms and expressions of excluding any equivalents, of any of the features described, or portions thereof, but it is recognized that various modifications are possible to the embodiments disclosed herein without departing from the scope of the invention. Accordingly, it is to be understood that the detailed description and the accompanying drawings are for purposes of showing the preferred and best embodiments of the invention and are not intended to limit the breadth of the present invention, but rather all modifications as would be obvious to one skilled in the art are intended to be included within the scope of the invention as defined within the following claims

The invention claimed is:

1. A disposable eye shield for covering and protecting the eye of a patient which includes an eye socket during treatment of the patient's facial area using light energy and electrical currents, said shield comprising:
    a metallic shell having a top surface and an underside surface with a peripheral edge extending outwardly around the shell to define an open area inside the shell, the edge having an underside surface;
    the metallic shell being formed to extend over and fit within the eye socket of the patient with the shell extending completely over the patient's eye;
    the metallic shell being of a metal foil capable of shielding the patient's eye from both light energy beams and electrical currents;
    an insulating layer extending over substantially the entire underside surface of the peripheral edge of the shell, the insulating layer having an adhesive on its underside surface to secure the shield to the patient's skin;
    a releasable paper layer covering the underside surface of the insulating layer to protect the adhesive on the insulating layer until the shield is ready to be used; and
    the insulating layer and paper layer each extending over the underside surface of the peripheral edge of the shell without blocking the open area inside the shell, thereby providing for each eye shield to be stacked one on top of another.

2. The disposable eye shield of claim 1 in which the metallic shell is of a material that is rigid.

3. The disposable eye shield of claim 1 in which the metallic shell is of a material that is flexible.

4. The disposable eye shield of claim 1 in which the insulating layer extends over the underside surface of the peripheral edge of the shell without blocking the open area inside the shell, and the paper layer extends over the entire underside surface of the shield, the paper layer being cross-cut inside of the peripheral edge thereby providing for each eye shield to be stacked one on top of another.

5. The disposable eye shield of claim 1 which the shield is color coded to distinguish different sizes or types of shields.

* * * * *